US00PP25357P3

(12) United States Plant Patent
Lommerse

(10) Patent No.: US PP25,357 P3
(45) Date of Patent: Mar. 17, 2015

(54) ***GAZANIA* PLANT NAMED 'LOMGAZWHTR'**

(50) Latin Name: *Gazania splendens*
Varietal Denomination: LOMGAZWHTR

(71) Applicant: Henry Lommerse, Mariahout (NL)

(72) Inventor: Henry Lommerse, Mariahout (NL)

(73) Assignee: Lommerse Holdings B.V. (NL)

( * ) Notice: Subject to any disclaimer, the term of this patent is extended or adjusted under 35 U.S.C. 154(b) by 108 days.

(21) Appl. No.: 13/815,085

(22) Filed: Jan. 30, 2013

(65) Prior Publication Data

US 2014/0215661 P1 Jul. 31, 2014

(51) Int. Cl.
*A01H 5/00* (2006.01)

(52) U.S. Cl.
USPC ..... Plt./334

(58) Field of Classification Search
CPC ..... A01H 5/00
USPC ..... Plt./334
See application file for complete search history.

*Primary Examiner* — Anne Grunberg

(57) ABSTRACT

A new and distinct *Gazania* cultivar named 'LOMGAZWHTR' is disclosed, characterized by compact plant habit, large flower size and unique tricolored flowers. The new variety is a *Gazania,* normally produced as an outdoor garden or container plant.

2 Drawing Sheets

Latin name of the genus and species: *Gazania splendens.*
Variety denomination: 'LOMGAZWHTR'.

BACKGROUND OF THE INVENTION

The new *Gazania* cultivar is a product of a planned breeding program conducted by the inventor, Henry Lommerse, in a commercial greenhouse in Mariahout, the Netherlands. The objective of the breeding program was to produce new *Gazania* varieties. The cross resulting in this new variety was made during June of 2007.

The seed parent is the unpatented, proprietary variety *Gazania* '8162/07'. The pollen parent is the unpatented, proprietary variety *Gazania* '5711/07'. The new variety was identified as a potentially interesting selection in Jul. 3, 2008, at a commercial greenhouse in Mariahout, the Netherlands.

Asexual reproduction of the new cultivar 'LOMGAZWHTR' by vegetative cuttings was first performed during May of 2009, at a commercial greenhouse in Mariahout, the Netherlands. Subsequent propagation has shown that the unique features of this cultivar are stable and reproduced true to type on successive generations.

SUMMARY OF THE INVENTION

The cultivar 'LOMGAZWHTR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOMGAZWHTR' These characteristics in combination distinguish 'LOMGAZWHTR' as a new and distinct *Gazania* cultivar:

1. Compact plant habit.
2. Large flower size.
3. Unique tricolored flower.

4. Flowers stay open during a long part of the day, including dark evening hours.
5. Commercially useful as garden plant.
6. Uniquely suited for container plant use.

PARENT COMPARISON

Plants of the new cultivar 'LOMGAZWHTR' are similar to plants of the seed parent, *Gazania* '8162/07' in most horticultural characteristics, however, plants of the new cultivar 'LOMGAZWHTR' produce larger flowers with more vivid coloration than the seed parent.

Plants of the new cultivar 'LOMGAZWHTR' are similar to plants of the pollen parent, *Gazania* '5711/07' in most horticultural characteristics, however, plants of the new cultivar 'LOMGAZWHTR' are more compact and flower earlier than the pollen parent.

COMMERCIAL COMPARISON

Plants of the new cultivar are best compared to the unpatented commercial variety *Gazania* 'Gazoo Yellow'. Plants of the new variety produce tricolored flower color compared to the yellow flower color of 'Gazoo Yellow'. Additionally, flowers of the new variety are open for a longer period and flower continuously, rather than sporadically.

BRIEF DESCRIPTION OF THE PHOTOGRAPHS

Figure 1:
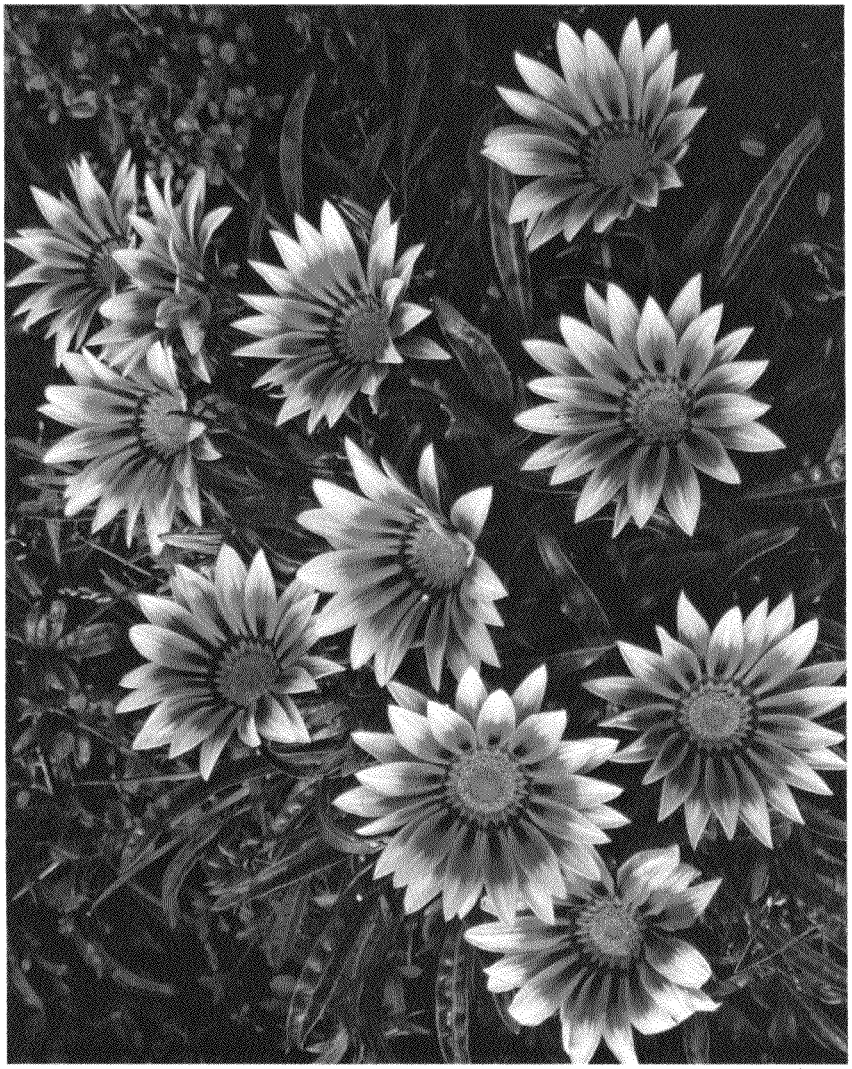

The accompanying photograph in FIG. 1 illustrates in full color a typical plant of 'LOMGAZWHTR' grown outdoors in Mariahout, the Netherlands, in in the ground in a trial field. Age of the plant photographed is approximately 6 months from a rooted cutting.

Figure 2:
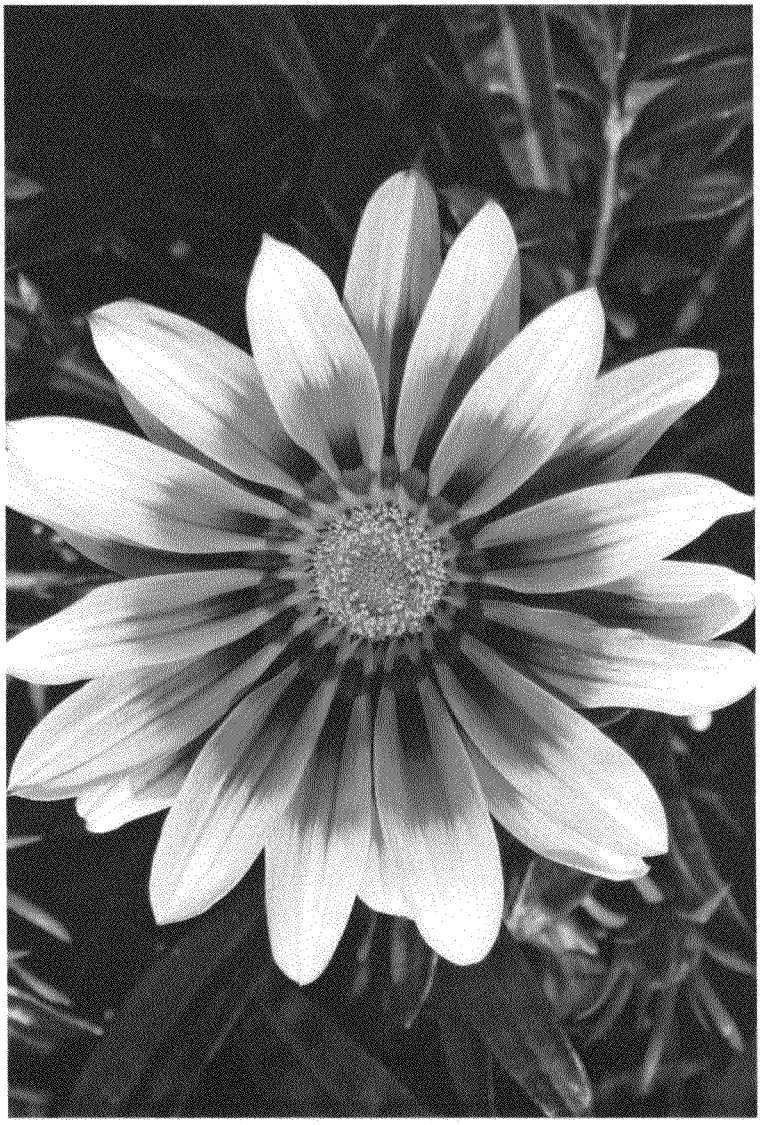

FIG. 2 illustrates in full color a typical inflorescence of 'LOMGAZWHTR'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'LOMGAZWHTR' plants grown in a commercial greenhouse in Mariahout, the Netherlands. The growing temperature ranged from 17° C. during the day to 15° C. during the night. The greenhouse is un-shaded, giving bright, normal sunlight conditions. Measurements and numerical values represent averages of typical plant types.

Botanical classification: *Gazania splendens* 'LOMGAZWHTR'.

PROPAGATION

Time to initiate roots: About 21 days at approximately 17° C.
Root description: Fine, freely branching.

PLANT

Age of plant described: 12 weeks from a rooted cutting.
Growth habit: Upright.
Height: Approximately 22 cm.
Plant spread: Approximately 40 cm.
Growth rate: On average 3 cm per week, depends on time of year.
Branching characteristics: No branching.

FOLIAGE

Leaf:
- *Arrangement.*—Irregularly whorled, basally emerging, single.
- *Average length.*—Approximately 13 cm.
- *Average width.*—Approximately 4 cm.
- *Shape of blade.*—Oblanceolate.
- *Apex.*—Acute.
- *Base.*—Attenuate.
- *Attachment.*—Stalked.
- *Margin.*—Entire.
- *Texture of top surface.*—Glabrous.
- *Texture of bottom surface.*—Glabrous.
- *Appearance top surface.*—Glossy.
- *Appearance bottom surface.*—Shiny.
- *Leaf internode length.*—Approximately 0.3 to 1 cm.
- *Color.*—Young foliage upper side: Near RHS Green 138 A. Young foliage under side: Near RHS Green 138 D. Mature foliage upper side: Near RHS Yellow-Green 147 A. Mature foliage under side: Near RHS Yellow-Green 147 D.
- *Type.*—Pinnate. Venation color upper side: Indistinguishable from leaf blade. Venation color under side: Indistinguishable from leaf blade.

Petiole:
- *Length.*—Average 3.0 cm.
- *Diameter.*—0.3 cm.
- *Pubescence.*—No.
- *Color.*—Near RHS Green 144A.

FLOWER

Natural blooming season: Spring and Summer, continuously flowering.

Flower form: Daisy-type composite inflorescence form. Inflorescences solitary. Ray and disc florets develop acropetally on a capitulum.

Bud:
- *Bud shape.*—Conical.
- *Bud length.*—Approximately 3 cm.
- *Bud diameter.*—Approximately 1 cm.
- *Bud color.*—Near RHS Green 144 A.

Inflorescence/flower:
- *Diameter of entire flower.*—Approximately 11.5 cm.
- *Depth of flower.*—Approximately 1.5 cm.
- *Width of disc.*—Approximately 2 cm.
- *Depth of disc.*—Approximately 1.5 cm.
- *Quantity per plant.*—Approximately 15 flowers and buds on a 12 week old plant.

Ray florets:
- *Number of ray florets.*—Avg. 20.
- *Length.*—Approximately 4 cm.
- *Width.*—Approximately 1.3 cm.
- *Apex.*—Acute.
- *Base.*—Attenuate.
- *Shape.*—Oblanceolate.
- *Margin.*—Entire.
- *Texture.*—Glabrous.
- *Aspect.*—Slightly curved.

Color:
- *Ray florets.*—Upper surface at first opening: Near RHS Yellow-White 158 D. Heavily streaked Yellow-Orange 22 A and Orange-Red N34A. Upper surface at maturity: Near RHS Yellow-White 158 C. Heavily streaked Yellow-Orange 22 A, Yellow-Orange 23 A and Orange-Red N34 A. Upper surface at fading: Near RHS Orange-White 159 C. Streaked Yellow-Orange 17A. Under surface at first opening: Near RHS Orange-White 159 D. Moderately streaked Yellow-Orange 22 A and Orange-Red N34A. Under surface at maturity: Near RHS Orange-White 159 C. Streaked Yellow-Orange 22 A. Under surface at fading: Near RHS Orange-White 159 C. Streaked Yellow-Range 15 B.
- *Disc florets.*—Number of Disc Florets: Approximately 195. Length: 1 to 1.5 cm. Width: 0.2 to 0.3 cm. Shape: Tubular. Margin: Wavy.

Color:
- *At first opening.*—Near RHS Yellow 13 B.
- *At maturity.*—Near RHS Yellow 13 C.
- *At fading.*—Near RHS Yellow 12 C.

Fragrance: No.

Peduncle:
- *Peduncle length.*—Approximately 15 cm.
- *Peduncle diameter.*—Approximately 1 cm.
- *Angle.*—Approximately 90 deg from center of whorl. (Upright).
- *Color.*—Near RHS Green 138 C.
- *Peduncle texture.*—Glabrous.

REPRODUCTIVE ORGANS

Disc florets:

*Androecium*.—Stamens: About 5. Anther shape: Linear. Anther length: Approximately 0.5 cm.

*Gynoecium*.—Pistil number: 1. Pistil shape: Needle. Pistil length: Approx. 0.5 cm. Style length: Approx. 0.5 cm.

Ray florets (if any reproductive structures present):

*Androecium*.—Not present.

*Gynoecium*.—Pistil number: 1. Pistil shape: Needle.

OTHER CHARACTERISTICS

Fruit/seed production: Moderate production of achene type seeds.

*Shape*.—Ovate.

*Color*.—Near RHS Grey-Brown 199B.

*Size*.—2 mm.

Disease/pest resistance: Good tolerance for the normal pests and diseases of *Gazania*.

Drought tolerance and cold tolerance: Very tolerant for dry conditions, tolerates temperatures from approximately 1° C. to above 40° C.

What is claimed is:

1. A new and distinct cultivar of *Gazania* plant named 'LOMGAZWHTR' as herein illustrated and described.

* * * * *